US012773574B2

(12) United States Patent
Hyvönen et al.

(10) Patent No.: US 12,773,574 B2
(45) Date of Patent: Oct. 27, 2026

(54) METHOD AND APPARATUS FOR STEREOTACTIC BODY RADIATION TREATMENT PLANNING AND ADMINISTRATION

(71) Applicant: Siemens Healthineers International AG, Steinhausen (CH)

(72) Inventors: Heini Hyvönen, Helsinki (FI); Jarkko Y. Peltola, Tuusula (FI); Christopher Boylan, Helsinki (FI); Emmi Ruokokoski, Helsinki (FI)

(73) Assignee: Siemens Healthineers International AG, Steinhausen (CH)

( * ) Notice: Subject to any disclaimer, the term of this patent is extended or adjusted under 35 U.S.C. 154(b) by 1127 days.

(21) Appl. No.: 17/853,395

(22) Filed: Jun. 29, 2022

(65) Prior Publication Data

US 2024/0001144 A1 Jan. 4, 2024

(51) Int. Cl.
*A61N 5/10* (2006.01)

(52) U.S. Cl.
CPC ......... *A61N 5/1031* (2013.01); *A61N 5/1064* (2013.01); *A61N 2005/1074* (2013.01)

(58) Field of Classification Search
CPC .... A61N 5/1031; A61N 5/1064; A61N 5/103; A61N 5/1071; A61N 2005/1074
See application file for complete search history.

(56) References Cited

U.S. PATENT DOCUMENTS

| | | | | |
|---|---|---|---|---|
| 2017/0087385 | A1* | 3/2017 | Miettinen | A61N 5/1071 |
| 2018/0193665 | A1 | 7/2018 | Kuusela | |
| 2018/0318606 | A1 | 11/2018 | Robinson | |
| 2020/0406060 | A1* | 12/2020 | Huth | A61N 5/103 |
| 2021/0379405 | A1 | 12/2021 | Huth | |
| 2022/0133401 | A1* | 5/2022 | O'Brien | A61B 18/1492 606/41 |

OTHER PUBLICATIONS

International Search Report and Written Opinion from International Patent No. PCT/EP2023/066828 dated Sep. 7, 2023; 15 pages.

* cited by examiner

*Primary Examiner* — Gerald Johnson
(74) *Attorney, Agent, or Firm* — Fitch, Even, Tabin & Flannery LLP

(57) ABSTRACT

A control circuit presents to a user an automatic radiation treatment plan optimizer that provides pre-existing accuracy input parameters and that includes an opportunity to select a stereotactic body radiation treatment planning mode in addition to other treatment planning modes. In response to a user selecting the stereotactic body radiation treatment planning mode, the control circuit automatically overrides at least one of the pre-existing accuracy input parameters when automatically optimizing a radiation treatment plan.

19 Claims, 6 Drawing Sheets

Fields

Isocenter 1

Position(DICOM): X:-6.77cm Y:5.55cm Z:1.68cm
Scale: ICE61217

| Field Name | | | Gantry[°] | Collimator[°] | MU |
|---|---|---|---|---|---|
| Field 1 | VMAT | SRS | 30.0° - 180.1° CCW | 272.5° | 2528.8 MU |
| Field 2 | VMAT | SRS | 180.1° - 30.0° CW | 280.0° | 1447.1 MU |
| Field 3 | VMAT | SRS | 30.0° - 180.1° CCW | 70.0° | 2031.0 MU |
| Total | | | | | |
| Total | | | | | 6006.9 MU |

103

FIG. 6

METHOD AND APPARATUS FOR STEREOTACTIC BODY RADIATION TREATMENT PLANNING AND ADMINISTRATION

TECHNICAL FIELD

These teachings relate generally to treating a patient's planning target volume with energy pursuant to an energy-based treatment plan and more particularly to optimizing a stereotactic body radiation treatment plan.

BACKGROUND

The use of energy to treat medical conditions comprises a known area of prior art endeavor. For example, radiation therapy comprises an important component of many treatment plans for reducing or eliminating unwanted tumors. Unfortunately, applied energy does not inherently discriminate between unwanted material and adjacent tissues, organs, or the like that are desired or even critical to continued survival of the patient. As a result, energy such as radiation is ordinarily applied in a carefully administered manner to at least attempt to restrict the energy to a given target volume. A so-called radiation treatment plan often serves in the foregoing regards.

A radiation treatment plan typically comprises specified values for each of a variety of treatment-platform parameters during each of a plurality of sequential fields. Treatment plans for radiation treatment sessions are often automatically generated through a so-called optimization process. As used herein, "optimization" will be understood to refer to improving a candidate treatment plan without necessarily ensuring that the optimized result is, in fact, the singular best solution. Such optimization often includes automatically adjusting one or more physical treatment parameters (often while observing one or more corresponding limits in these regards) and mathematically calculating a likely corresponding treatment result (such as a level of dosing) to identify a given set of treatment parameters that represent a good compromise between the desired therapeutic result and avoidance of undesired collateral effects.

Stereotactic body radiation treatment comprises a known approach to administering therapeutic radiation. Stereotactic body radiation treatment finds particular use when treating small-sized treatment targets. Non-stereotactic body conventional radiation treatment typically utilizes relatively low doses of radiation per fraction of the total dose. In stereotactic body radiation treatment, however, the doses per fraction are higher (often considerably higher) by way of comparison. For example, conventional therapy might provide for 25 fractions of 2 Gy per fraction whereas stereotactic body radiation treatment might provide for 5 fractions of 7.5 Gy per fraction.

The applicant has determined that available approaches to automatically generating a radiation treatment plan do not necessarily provide satisfactory results in all application settings when seeking to generate a plan to administer a stereotactic body radiation treatment. The applicant has determined that this is due, at least in part, to the presumptions and considerations that differentiate stereotactic body radiation treatment from other radiation treatment modalities.

BRIEF DESCRIPTION OF THE DRAWINGS

The above needs are at least partially met through provision of the method and apparatus for stereotactic body radiation treatment planning and administration described in the following detailed description, particularly when studied in conjunction with the drawings, wherein:

FIG. 6 comprises a screen shot as configured in accordance with various embodiments of these teachings.

Figure 1:
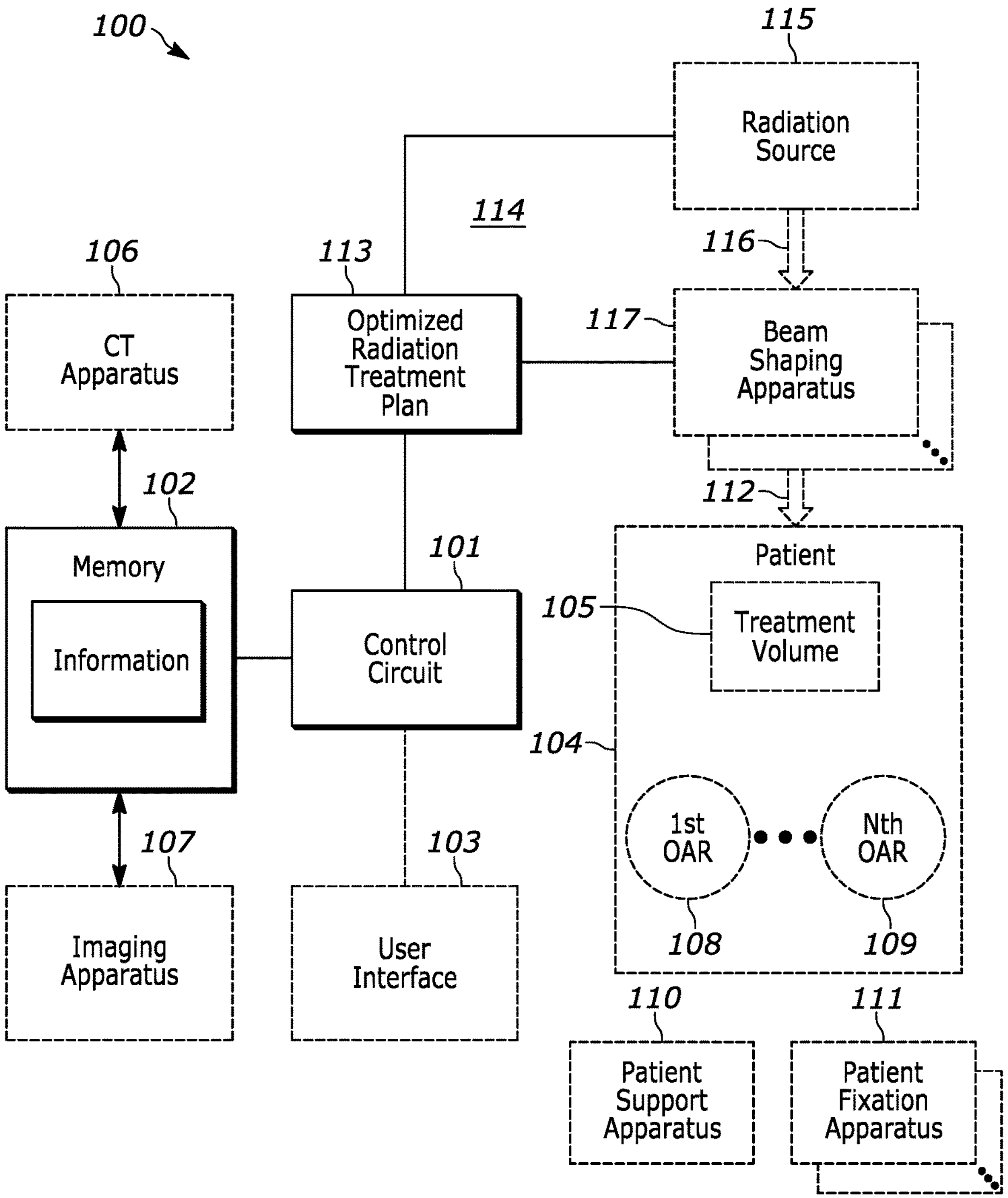
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, pursuant to these various embodiments a control circuit presents to a user an automatic radiation treatment plan optimizer that provides pre-existing accuracy input parameters and that includes an opportunity to select a stereotactic body radiation treatment planning mode in addition to other treatment planning modes. In response to a user selecting the stereotactic body radiation treatment planning mode, the control circuit automatically overrides at least one of the pre-existing accuracy input parameters when automatically optimizing a radiation treatment plan.

By one approach, automatically overriding one or more pre-existing accuracy input parameters comprises, at least in part, automatically accessing an alternative parameter set. That alternative parameter set may include, at least in part, parameters corresponding to at least one or both of sampling of a structure model and dose calculation resolution. The parameter set may also include, in lieu of the foregoing or in combination therewith, parameters corresponding to at least one or both of treatment machine configuration parameters and treatment limits parameters (such as, but not limited to, a maximum dose rate limit and a maximum allowed monitor units limit). The accessed information may be substituted for the preexisting information or may be presented or otherwise made available as a supplement.

These teachings will accommodate also presenting to the user an opportunity to modify at least one parameter in the aforementioned alternative parameter set.

In cases where the automatic radiation treatment plan optimizer is configured to optimize radiation beam geometry, by one approach these teachings will accommodate automatically modifying optimization of the radiation beam geometry with respect to at least one of how many fields are generated and how much arc length is covered by arc geometry when the user selects the aforementioned stereotactic body radiation treatment planning mode.

These teachings are highly flexible in practice and will accommodate, for example, also automatically modifying optimization objectives with respect to how quickly radiation dosing is required to fall-off outside a target volume, how many Monitor Units are used to generate an administered dose, and/or a required degree of dose distribution homogeneity inside a target volume in response to the user selecting the stereotactic body radiation treatment planning mode.

So configured, an automatic radiation treatment plan optimizer can efficiently and reliably generate a clinically efficacious and acceptable stereotactic body radiation treatment plan. Such a plan, for example, will tend to avoid extra leaf modulation, minimize treatment time, and offer good dosimetric accuracy.

These and other benefits may become clearer upon making a thorough review and study of the following detailed description. Referring now to the drawings, and in particular to FIG. 1, an illustrative apparatus 100 that is compatible with many of these teachings will first be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to information such as optimization information for a particular patient, information regarding a particular radiation treatment platform, accuracy input parameters, and an alternative parameter set as described herein, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

If desired the control circuit 101 can also operably couple to a network interface (not shown). So configured the control circuit 101 can communicate with other elements (both within the apparatus 100 and external thereto) via the network interface. Network interfaces, including both wireless and non-wireless platforms, are well understood in the art and require no particular elaboration here.

By one approach, a computed tomography apparatus 106 and/or other imaging apparatus 107 as are known in the art can source some or all of any desired patient-related imaging information.

In this illustrative example the control circuit 101 is configured to ultimately output an optimized energy-based treatment plan (such as, for example, an optimized radiation treatment plan 113). This energy-based treatment plan typically comprises specified values for each of a variety of treatment-platform parameters during each of a plurality of sequential exposure fields. In this case the energy-based treatment plan is generated through an optimization process, examples of which are provided further herein.

By one approach the control circuit 101 can operably couple to an energy-based treatment platform 114 that is configured to deliver therapeutic energy 112 to a corresponding patient 104 in accordance with the optimized energy-based treatment plan 113. These teachings are generally applicable for use with any of a wide variety of energy-based treatment platforms/apparatuses. In a typical application setting the energy-based treatment platform 114 will include an energy source such as a radiation source 115 of ionizing radiation 116.

By one approach this radiation source 115 can be selectively moved via a gantry along an arcuate pathway (where the pathway encompasses, at least to some extent, the patient themselves during administration of the treatment). The arcuate pathway may comprise a complete or nearly complete circle as desired. By one approach the control circuit 101 controls the movement of the radiation source 115 along that arcuate pathway, and may accordingly control when the radiation source 115 starts moving, stops moving, accelerates, de-accelerates, and/or a velocity at which the radiation source 115 travels along the arcuate pathway.

As one illustrative example, the radiation source 115 can comprise, for example, a radio-frequency (RF) linear particle accelerator-based (linac-based) x-ray source. A linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons.

A typical energy-based treatment platform 114 may also include one or more support apparatuses 110 (such as a couch) to support the patient 104 during the treatment session, one or more patient fixation apparatuses 111, a gantry or other movable mechanism to permit selective movement of the radiation source 115, and one or more energy-shaping apparatuses (for example, beam-shaping apparatuses 117 such as jaws, multi-leaf collimators, and so forth) to provide selective energy shaping and/or energy modulation as desired.

In a typical application setting, it is presumed herein that the patient support apparatus 110 is selectively controllable to move in any direction (i.e., any X, Y, or Z direction) during an energy-based treatment session by the control circuit 101. As the foregoing elements and systems are well understood in the art, further elaboration in these regards is not provided here except where otherwise relevant to the description.

Figure 2:
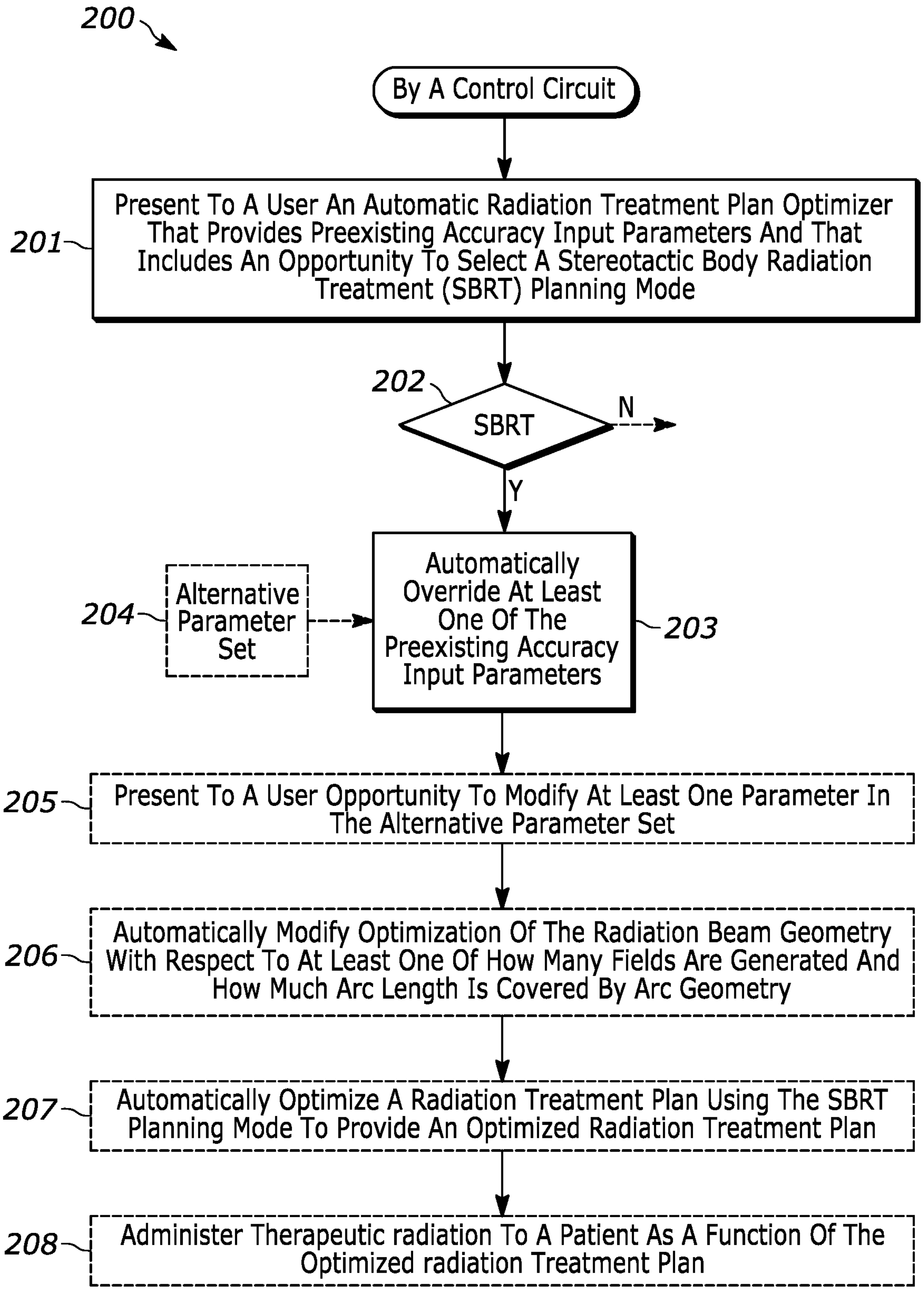
FIG. 2 comprises a flow diagram as configured in accordance with various embodiments of these teachings.

Referring now to FIG. 2, a process 200 that can be carried out, for example, in conjunction with the above-described application setting (and more particularly via the aforementioned control circuit 101) will be described. Generally speaking, this process 200 serves to facilitate generating an optimized stereotactic body radiation treatment plan to thereby facilitate treating a particular patient with therapeutic radiation using a particular radiation treatment platform using stereotactic body radiation treatment.

Figure 3:
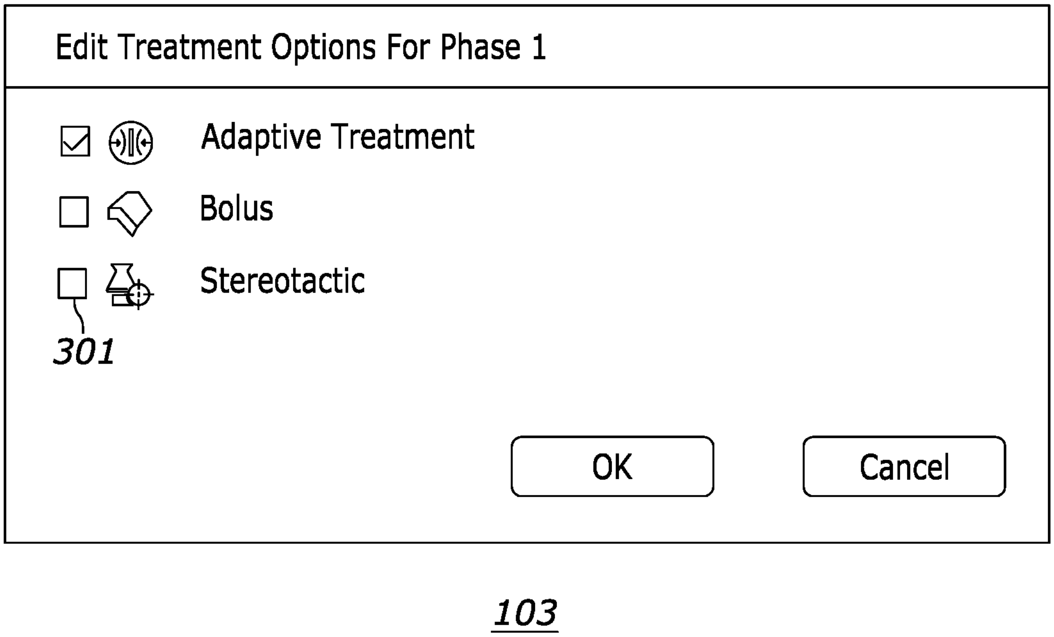
FIG. 3 comprises a screen shot as configured in accordance with various embodiments of these teachings.

At block 201, this process 200 provides for presenting to a user an automatic radiation treatment plan optimizer that provides pre-existing accuracy input parameters for non-stereotactic body radiation treatment and that also includes an opportunity to select a stereotactic body radiation treatment planning mode. This opportunity may be presented, for example, via the aforementioned user interface 103 and may comprise for example, a user-assertable virtual button. FIG. 3 provides an illustrative example in these regards where the opportunity comprises a checkbox 301 that a user can select/check in order to select the stereotactic body radiation treatment planning mode.

At block 202, and in response to detecting that the user has selected the stereotactic body radiation treatment planning mode, at block 203 this process 200 provides for automatically overriding at least one of the aforementioned pre-existing accuracy input parameters to be otherwise used when automatically optimizing a radiation treatment plan. (In the absence of detecting the foregoing trigger event, this process 200 can accommodate any of a variety of responses. Examples of responses can include temporal multitasking (pursuant to which the control circuit 101 conducts other tasks before returning to again monitor for the user assertion) as well as simply continually looping back to essentially continuously monitor for the trigger event. These teachings will also accommodate supporting this detection activity via a real-time interrupt capability.)

Figure 4:
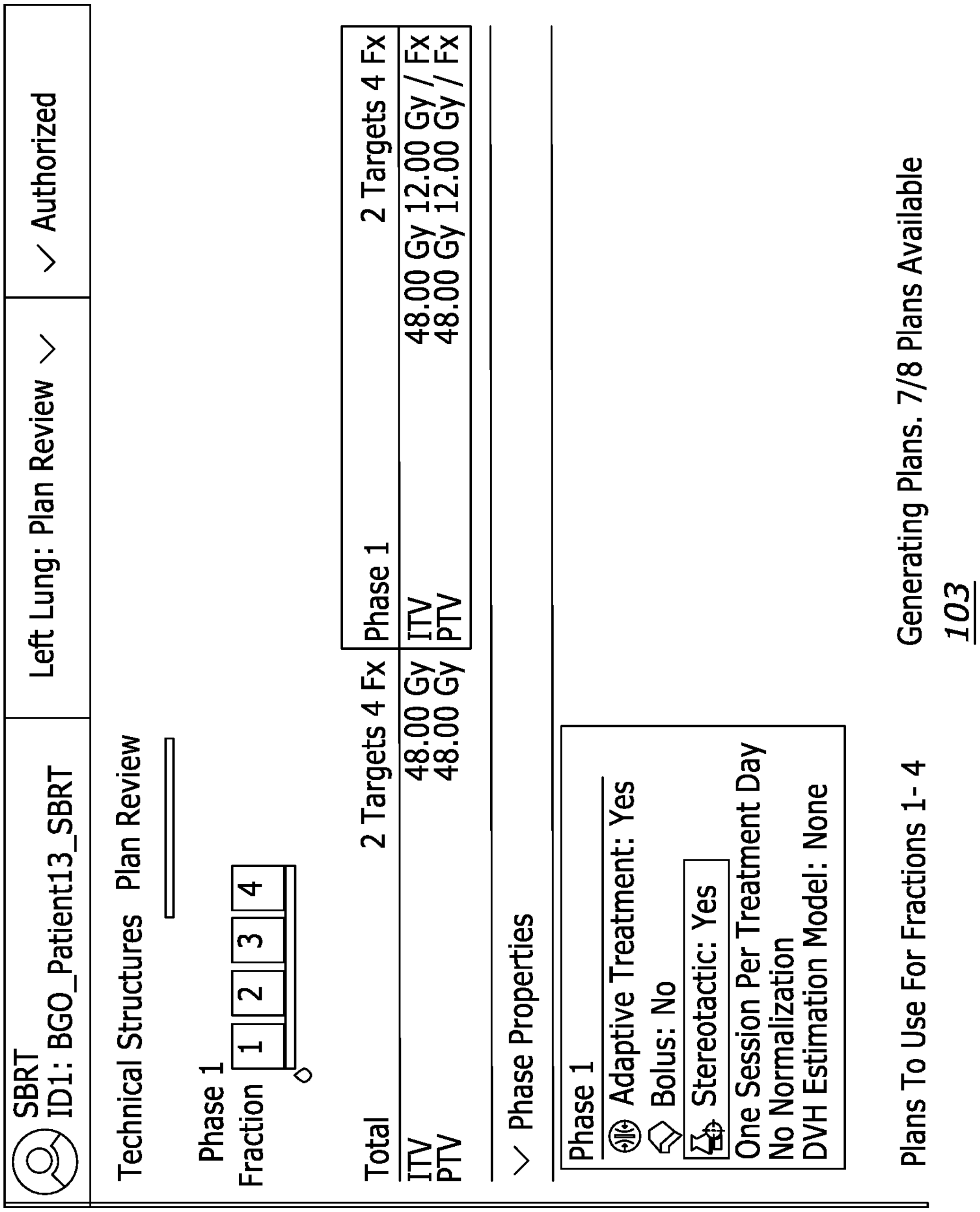
FIG. 4 comprises a screen shot as configured in accordance with various embodiments of these teachings.

FIG. 4 provides an illustrative example of a screen shot for the user interface 103 depicting plan review information when in the stereotactic body radiation treatment planning mode. The presented information shows, for example, that a given phase 1 treatment provides for four fractional treatments of 12 Gy per fraction for each of two treatment targets (i.e., targets denominated as ITV and PTV) that are each intended to receive a total dose of 48 Gy. This combination of only a few fractions coupled with relatively high doses is typical of stereotactic body radiation treatment.

By one approach, automatically overriding one or more of the pre-existing accuracy input parameters comprises, at least in part, automatically accessing an optional alternative parameter set 204. These teachings will accommodate a variety of different contents for this alternative parameter set 204. Examples include, but are not limited to, any or all of the sampling of a structure model, dose calculation resolution, treatment machine configuration parameters, and treatment limits parameters such as a maximum dose rate limit and/or a maximum allowed Monitor Units limit.

By one approach, automatically overriding a pre-existing accuracy input parameter can comprise automatically substituting the corresponding contents of such an alternative parameter set 204. By another approach, the user may be responsively provided with an opportunity to select a particular alternative parameter set from a plurality of different alternative parameter sets having at least somewhat differing contents. Different alternative parameter sets may be provided to accommodate, for example, different kinds of treatment targets and/or different regions of a patient's body that contain the treatment target.

As provided at optional block 205, these teachings will accommodate also presenting to the user an opportunity to modify at least one parameter in the aforementioned alternative parameter set 204.

Figure 5:
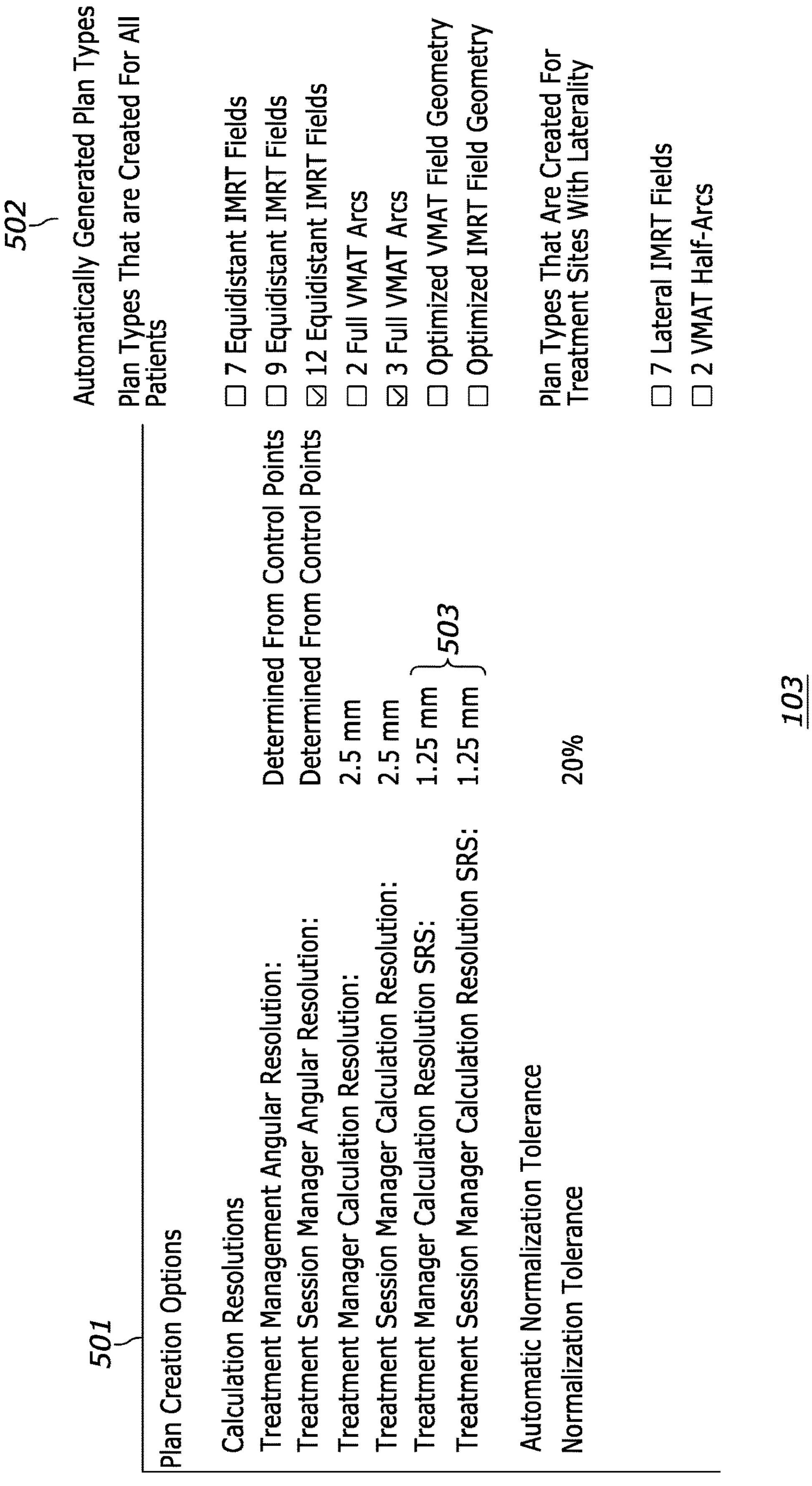
FIG. 5 comprises a screen shot as configured in accordance with various embodiments of these teachings.

FIG. 5 provides an illustrative example in these regards. In this view, a number of plan creation options 501 are supported by these teachings. For standard planning purposes, fractional planning dose calculation resolutions of 2.5 mm (as illustrated) or 3 mm (not shown) are available and can comprise a part of the aforementioned preexisting accuracy input parameters. Also available, however, is a resolution value of 1.25 mm (as denoted at reference numeral 503), which is a resolution value often well suited to a stereotactic body radiation treatment planning mode.

FIG. 5 also illustrates that the user interface 103 can provide a variety of automatically generated plan types 502 that will effected upon initiating the optimization/plan generation process. These teachings would also support having separate plan type options for the stereotactic mode. A user could, for example, select 12 Field IMRT for stereotactic cases and 7 Field IMRT for non-stereotactic cases. As another example, a user could have non-coplanar treatment plan options available.in the selection (for example, for treatment plans that include treatment couch rotation or other movement).

In some cases, the automatic radiation treatment plan optimizer may be configured to optimize radiation beam geometry. In such a case, and if desired, at optional block 206 this process 200 can provide for automatically modifying optimization of the radiation beam geometry. The latter may comprise, for example, modifying optimization of the radiation beam geometry with respect to at least one of how many fields are generated and/or how much arc length is covered by arc geometry. Overall arc length can be increased by, for example, increasing the number of arcs. By one approach, the number of fields and overall arc coverage can be optimized in stereotactic body radiation treatment mode based on the dose delivered in one treatment session (i.e., one dose fraction). For example, the number of fields may be increased when the dose exceeds a given threshold such as 20 Gy per fraction. FIG. 6 presents an illustrative example where specific gantry positions, collimator settings, and Monitor Unit values are specified for each of three separate fields.

These teachings will accommodate other responsive actions when a user selects the stereotactic body radiation treatment planning mode. As one non-limiting example in these regards, this process 200 can provide for automatically modifying optimization objectives when automatically optimizing the radiation treatment plan with respect to at least one of how quickly radiation dosing is required to fall off outside a target volume, how many Monitor Units are used to generate an administered dose, and/or a required degree of dose distribution homogeneity inside a target volume. Note, for example, that a typical non-stereotactic body radiation treatment mode seeks to achieve a certain homogeneity in the target dose distribution by, for example, keeping a maximum dose value under 107% of the dose prescription value. In stereotactic body radiation treatment, however, the target dose can be considerably higher (such as 130% or 150% of the dose prescription value) and these teachings can accommodate that circumstance by allowing higher dose in a target volume while allowing, for example, a steeper drop off of dosing beyond the target itself.

At optional block 207, this process 200 can provide for automatically optimizing a radiation treatment plan using the aforementioned stereotactic body radiation treatment planning mode to thereby provide a corresponding resultant optimized radiation treatment plan 113. At optional block 208, this process 200 can then provide for administering therapeutic radiation to a patient as a function of that optimized radiation treatment plan 113.

So configured, and as an illustrative example, a user who has set up their normal intent, including a prioritized list of clinical goals, can launch an automated planning program. Treatment field set up for the planning can be read from a template or generated automatically by a separate beam geometry optimization algorithm. When automatically generating beam geometry, the above-described stereotactic body radiation treatment mode will change the algorithm's behavior so that the beam geometries produced are suitable for high fraction dose use cases. For intensity-modulated radiation therapy (IMRT) cases this can correspond to how many fields are generated. For volumetric modulated arc therapy (VMAT) cases, this can correspond to how much arc length is covered by the generated fields. In lieu of the foregoing or in combination therewith, suitable automatically-generated beam geometry may include rotating (or otherwise moving) a patient support surface (such as a couch) relative to the radiation source in stereotactic plans. The latter approach would allow fields/arcs to enter the patient's body over a wider range and may also improve dose fall off and thereby reduce high doses to adjacent organs. Generally speaking, these teachings will accommodate changing all input field control point properties when selecting the stereotactic body radiation treatment mode if desired.

Continuing with this example, the stereotactic body radiation treatment mode can change how the automatic plan optimization algorithm proceeds even when other input stays the same. At least some of the dose characteristics that constitute a good plan can be achieved by setting extra objectives and clinical goals for either given input structures or for algorithmically-generated extra structures. By one approach, these extra controls can be prioritized in accordance with the given input goals.

By one approach, the algorithm will emphasize the dose fall off with respect to the target. This may include using so-called ring structures at, for example, 1 cm, 2 cm, 4 cm, or similar distances beyond each target's periphery. The generated ring structures and the corresponding dose goals are going to be different from what would otherwise be used in standard fractionation cases.

These teachings can also change how homogenous the dose inside the target needs to be. In a standard fractionation case, the maximum dose inside a target is typically required to be less than 107% of the prescribed dose. In the stereotactic body radiation treatment mode, however, the maximum dose is allowed to be higher (such as 120% higher, 130% higher, 150% higher, and so forth).

These and potentially other extra controls are prioritized differently in the stereotactic body radiation treatment mode as compared to a standard mode. Generally speaking, in the stereotactic body radiation treatment mode the optimization algorithm aims for low Monitor Units and low leaf modulation. Such results can be achieved, for example, by using strong fluence smoothing objectives for IMRT planning. For VMAT planning this can be achieved by using different initial leaf configuration starting points and stronger objectives for controlling adjacent leaf movement.

Those skilled in the art will recognize that a wide variety of modifications, alterations, and combinations can be made with respect to the above-described embodiments without departing from the scope of the invention, and that such modifications, alterations, and combinations are to be viewed as being within the ambit of the inventive concept.

What is claimed is:

1. A method comprising:

by a control circuit:

presenting to a user an automatic radiation treatment plan optimizer that provides preexisting accuracy input parameters, which include at least one fractional planning dose calculation resolution expressed in linear measurement units, and that includes an opportunity to select a stereotactic body radiation treatment (SBRT) planning mode;

in response to a user selecting the SBRT planning mode, automatically overriding at least one of the preexisting accuracy input parameters by overriding the least one fractional planning dose calculation resolution when automatically optimizing a radiation treatment plan.

2. The method of claim 1 wherein automatically overriding at least one of the preexisting accuracy input parameters comprises, at least in part, automatically accessing an alternative parameter set.

3. The method of claim 2 wherein the alternative parameter set includes, at least in part, parameters corresponding to both sampling of a structure model and dose calculation resolution.

4. The method of claim 2 further comprising:

presenting to a user an opportunity to modify at least one parameter in the alternative parameter set.

5. The method of claim 2 wherein the alternative parameter set includes, at least in part, parameters corresponding to at least one of treatment machine configuration parameters and treatment limits parameters.

6. The method of claim 2 wherein the alternative parameter set includes, at least in part, parameters corresponding both treatment machine configuration parameters and treatment limits parameters.

7. The method of claim 6 wherein the treatment limits parameters comprise, at least in part, a maximum dose rate limit and a maximum allowed monitor units limit.

8. The method of claim 1, wherein when the automatic radiation treatment plan optimizer is configured to optimize radiation beam geometry, in response to a user selecting the SBRT planning mode, automatically modifying optimization of the radiation beam geometry with respect to at least one of how many fields are generated, how much arc length is covered by arc geometry, and patient support surface movement.

9. The method of claim 1 further comprising:
automatically optimizing a radiation treatment plan using the SBRT planning mode to provide an optimized radiation treatment plan;
administering therapeutic radiation to a patient as a function of the optimized radiation treatment plan.

10. The method of claim 1 further comprising, in response to a user selecting the SBRT planning mode, automatically modifying optimization objectives when automatically optimizing the radiation treatment plan with respect to at least one of how quickly radiation dosing is required to fall-off outside a target volume, how many Monitor Units are used to generate an administered dose, and a required degree of dose distribution homogeneity inside a target volume.

11. An apparatus comprising:
a control circuit configured to:
present to a user an automatic radiation treatment plan optimizer that provides preexisting accuracy input parameters, which include at least one fractional planning dose calculation resolution expressed in linear measurement units, and that includes an opportunity to select a stereotactic body radiation treatment (SBRT) planning mode;
in response to a user selecting the SBRT planning mode, automatically override at least one of the preexisting accuracy input parameters by overriding the least one fractional planning dose calculation resolution when automatically optimizing a radiation treatment plan.

12. The apparatus of claim 11 wherein the control circuit is configured to automatically override at least one of the preexisting accuracy input parameters by, at least in part, automatically accessing an alternative parameter set.

13. The apparatus of claim 12 wherein the alternative parameter set includes, at least in part, parameters corresponding to both sampling of a structure model and dose calculation resolution.

14. The apparatus of claim 12 wherein the control circuit is further configured to:
present to a user an opportunity to modify at least one parameter in the alternative parameter set.

15. The apparatus of claim 12 wherein the alternative parameter set includes, at least in part, parameters corresponding to at least one of treatment machine configuration parameters and treatment limits parameters.

16. The apparatus of claim 12 wherein the alternative parameter set includes, at least in part, parameters corresponding both treatment machine configuration parameters and treatment limits parameters.

17. The apparatus of claim 16 wherein the treatment limits parameters comprise, at least in part, a maximum dose rate limit and a maximum allowed monitor units limit.

18. The apparatus of claim 11, wherein the control circuit is further, configured to when the automatic radiation treatment plan optimizer is configured to optimize radiation beam geometry, and in response to a user selecting the SBRT planning mode, automatically modify optimization of the radiation beam geometry with respect to at least one of how many fields are generated, how much arc length is covered by arc geometry, and patient support surface movement.

19. The apparatus of claim 11 wherein the control circuit is further configured to:
automatically optimize a radiation treatment plan using the SBRT planning mode to provide an optimized radiation treatment plan;
administer therapeutic radiation to a patient as a function of the optimized radiation treatment plan.

* * * * *